US012332232B1

(12) United States Patent
Lv et al.

(10) Patent No.: US 12,332,232 B1
(45) Date of Patent: Jun. 17, 2025

(54) CRUDE OIL TRANSPORTATION DRAG-REDUCING AGENT TESTING LOOP TEST BENCH AND A USE METHOD THEREOF

(71) Applicant: Ningbo Institute of Dalian University of Technology, Ningbo (CN)

(72) Inventors: Xin Lv, Beijing (CN); Huiyong Liang, Pizhou (CN); Shi Shen, Liaoyang (CN); Tao Liu, Linyi (CN); Xingyu Lu, Taiyuan (CN); Shuangqing Zhang, Hefei (CN); Linan Zhao, Beipiao (CN)

(73) Assignee: Ningbo Institute of Dalian University of Technology, Ningbo (CN)

( * ) Notice: Subject to any disclaimer, the term of this patent is extended or adjusted under 35 U.S.C. 154(b) by 0 days.

(21) Appl. No.: 19/033,754

(22) Filed: Jan. 22, 2025

(30) Foreign Application Priority Data

Apr. 8, 2024 (CN) .......................... 202410414340.2

(51) Int. Cl.
  *G01N 33/30* (2006.01)
  *G01N 33/28* (2006.01)
(52) U.S. Cl.
  CPC ......... *G01N 33/30* (2013.01); *G01N 33/2823* (2013.01); *G01N 33/2888* (2013.01)
(58) Field of Classification Search
  CPC . G01N 33/2888; G01N 33/30; G01N 33/2823
  See application file for complete search history.

(56) References Cited

U.S. PATENT DOCUMENTS

2020/0080391 A1* 3/2020 Marlatt ................ E21B 21/062
2021/0198557 A1* 7/2021 Nizamidin ............. E21B 43/26
2023/0063437 A1* 3/2023 Bu .......................... E21B 33/13

OTHER PUBLICATIONS

Dalian University of Technology Ningbo Research Institute (Applicant), Replacement claims (allowed) of CN202410414340.2, Sep. 3, 2024.
CNIPA, Notification to grant patent right for invention in CN202410414340.2, Sep. 16, 2024.

* cited by examiner

*Primary Examiner* — Paul M. West
(74) *Attorney, Agent, or Firm* — Hemisphere Law, PLLC; Zhigang Ma

(57) ABSTRACT

A crude oil transportation drag-reducing agent testing loop test bench and its use method is provided. The test bench includes a gas supply and pressurization system, a pressurized storage tank system, a pipeline testing system, a reflux and circulation system, a valve switching system, a heating and insulation testing system, and a sensor testing system. The test bench can evaluate the performance of drag-reducing agents in transportation pipeline devices within a laboratory setting, and further inspect, evaluate, and test the effective performance of different proportions and types of drag-reducing agents. The test bench also ensures the safety of experimental test, reduces testing costs, avoids the production of large amounts of waste liquid, and minimizes test space.

8 Claims, 12 Drawing Sheets

CRUDE OIL TRANSPORTATION DRAG-REDUCING AGENT TESTING LOOP TEST BENCH AND A USE METHOD THEREOF

CROSS-REFERENCE TO RELATED APPLICATION

This application claims priority to Chinese Patent Application No. 202410414340.2, filed on Apr. 8, 2024, which is herein incorporated by reference in its entirety.

TECHNICAL FIELD

The disclosure relates to the field of drag-reducing agent transportation testing technologies, and more particularly to a crude oil transportation drag-reducing agent testing loop test bench and a use method thereof.

BACKGROUND

Adding certain drag-reducing agent materials to crude oil and refined oil transportation pipelines can reduce pipeline friction, effectively improve transportation efficiency, reduce costs, and also benefit the safe operation of pipelines. In order to better test performance indicators of different drag-reducing agents and to select and evaluate the different drag-reducing agents, transportation pipeline testing devices are typically used to conduct test parameters.

FIG. 1 illustrates a schematic diagram of an indoor testing loop process flow.

1: a nitrogen cylinder group, configured (i.e., structured and arranged) to pressurize a nitrogen pressure storage tank 2. Other nitrogen sources, such as nitrogen trucks, can also be used to replace the nitrogen cylinder group.

3: constant pressure regulating valves, arranged in two groups in parallel, with one valve per group. A constant pressure regulating valve is connected to the two groups in series to ultimately control the pressure. A pressure adjustment range is 0 megapascal (MPa) to 1.2 MPa. The constant pressure regulating valves are configured to ensure that the pressure in the oil transportation pressure buffer tank remains stable at a set value.

4: an oil transportation pressure buffer tank, with a set pressure of 1.6 MPa and a volume of 0.1 cubic meters ($m^3$). The oil transportation pressure buffer tank is configured to hold a liquid used for evaluation and also serves as a power source for the test pipelines.

5: a first testing loop, with an inner diameter of 6.35 millimeters (mm), 4 pressure measurement points on the pipe, and a test length of 24 meters (m). The first testing loop is installed horizontally, with straight pipe sections in front of and behind the pressure measurement points not less than 30 times the pipe diameter.

6: a second testing loop, with an inner diameter of 12.7 mm, 6 pressure measurement points on the pipe, and a test length of 24 m. The installation method and requirements of the second testing loop are the same as the first testing loop.

7: a third testing loop, with an inner diameter of 25.4 mm, 4 pressure measurement points on the pipe, and a test length of 24 m. The installation method and requirements of the third testing loop are the same as the first testing loop.

8: a reflux pipeline, with an inner diameter of 25.4 mm. The liquid in a reflux tank flows back to the oil transportation pressure buffer tank through the reflux pipeline.

9: a pressure sensor. The pressure sensor can display locally, with a measurement range of 0 MPa to 1.0 MPa and an accuracy of 0.1%.

10: a weight flow meter. The weight flow meter is installed on a manifold of the first, second and third testing loops, and measures the flow through the first, second and third testing loops with an accuracy of 0.1%.

11: the reflux tank, with a volume of 1 $m^3$. The reflux tank is located at an end of the testing loops, and the liquid inside the reflux tank can be returned to the oil transportation pressure buffer tank through a gear pump via the reflux pipeline.

12: a reflux pump, with a rated flow rate of 2.4 cubic meters per hour ($m^3/h$). The reflux pump is configured to return the liquid from the reflux tank to the oil transportation pressure buffer tank, and shear and destroy the drag-reducing agent in the liquid medium after the test is completed.

13: a flow control valve. The flow control valve is remotely controlled for adjustment, with an accuracy of 0.1%, used to regulate the flow in a test section to maintain it at a constant value.

In the indoor testing loop process equipment described above, while evaluating the performance of the drag-reducing agents in transportation pipeline devices within the laboratory, how to further inspect, evaluate, and test the effective performance of different proportions and types of drag-reducing agents, while also ensuring the safety of experimental test, reducing testing costs, and avoiding the production of large amounts of waste liquid, is a technical problem that urgently needs to be addressed.

SUMMARY

A purpose of the disclosure is to provide a crude oil transportation drag-reducing agent testing loop test bench and a use method thereof, to evaluate the performance of drag-reducing agents in transportation pipeline devices within a laboratory, and further inspect, evaluate and test the effective performance of different proportions and types of drag-reducing agents, considering the safety of experimental test, reducing testing costs, avoiding the production of large amounts of waste liquid, and minimizing test space.

In order to achieve above purpose, the disclosure provides the crude oil transportation drag-reducing agent testing loop test bench and the use method thereof, with the following technical solutions.

In a first aspect, the crude oil transportation drag-reducing agent testing loop test bench includes: a gas supply and pressurization system, a pressurized storage tank system, a pipeline testing system, a reflux and circulation system, a valve switching system, a heating and insulation testing system, and a sensor testing system.

The gas supply and pressurization system is connected to a second pipeline through a first pipeline, the second pipeline is connected to a first end of the pressurized storage tank system, and a second end of the pressurized storage tank system is connected to a third pipeline, the third pipeline is connected to a fourth pipeline, a fifth pipeline, a sixth pipeline, a seventh pipeline, and an eighth pipeline, and the fourth pipeline is connected to a first air compressor.

The pipeline testing system includes a first test pipeline, a second test pipeline and a third test pipeline. The sixth pipeline, the seventh pipeline and the eighth pipeline are respectively connected to the third test pipeline, the second test pipeline and the first test pipeline, an end of the second test pipeline is connected to an end of the third test pipeline through a ninth pipeline, and an end of the first test pipeline is connected to a tenth pipeline.

The reflux and circulation system includes a reflux tank and a reflux pump. The tenth pipeline is connected to the reflux tank, the reflux tank is connected to a liquid preparation tank through an eleventh pipeline, the eleventh pipeline is connected to the fifth pipeline, the reflux pump is disposed on the eleventh pipeline, the reflux tank is connected to a second air compressor through a twelfth pipeline, and an upper end of the reflux tank is provided with a thirteenth pipeline.

The valve switching system includes: a manual valve group and an electromagnetic valve group.

The manual valve group includes a first manual valve, a second manual valve, a third manual valve, a fourth manual valve, a fifth manual valve, a sixth manual valve, a seventh manual valve, an eighth manual valve, a ninth manual valve, a tenth manual valve and an eleventh manual valve. The first manual valve, the second manual valve and the third manual valve are respectively disposed on the sixth pipeline, the seventh pipeline and the eighth pipeline. The fourth manual valve and the fifth manual valve are disposed on a ninth pipeline. The sixth manual valve, the seventh manual valve and the eighth manual valve are disposed on the tenth pipeline. The ninth manual valve is disposed on the thirteenth pipeline. The tenth manual valve is disposed on the third pipeline. The eleventh manual valve is disposed on a fourteenth pipeline connected to the first pipeline.

The electromagnetic valve group includes a first electromagnetic valve, a second electromagnetic valve, a third electromagnetic valve, a fourth electromagnetic valve, a fifth electromagnetic valve, a sixth electromagnetic valve, a seventh electromagnetic valve and an eighth electromagnetic valve. The first electromagnetic valve is disposed on the third pipeline. The second electromagnetic valve is disposed on the second pipeline. The third electromagnetic valve is disposed on the fourth pipeline. The fourth electromagnetic valve is disposed on the twelfth pipeline. The fifth electromagnetic valve and the eighth electromagnetic valve are disposed on the eleventh pipeline. The sixth electromagnetic valve is disposed on the fifth pipeline. The seventh electromagnetic valve is disposed on a fifteenth pipeline. An end of the fifteenth pipeline is connected to the eleventh pipeline, and another end of the fifteenth pipeline is connected to the reflux tank.

The heating and insulation testing system includes a first insulation layer and a second insulation layer. The first insulation layer is disposed on an outer side of the pressurized storage tank system, and the second insulation layer is disposed on an outer side of the pipeline testing system.

The sensor testing system includes temperature sensors, pressure sensors, differential pressure sensors, and a flow sensor. The temperature sensors, the pressure sensors, and the differential pressure sensors are disposed on the pipeline testing system to collect temperature, differential pressure and pressure signals from the first, second and third test pipelines, and the flow sensor is disposed on the sixth pipeline.

In an embodiment, the crude oil transportation drag-reducing agent testing loop test bench further includes a data acquisition and control system. A signal output end of the data acquisition and control system is connected to a signal input end of the valve switching system, and a signal input end of the data acquisition and control system is connected to a signal output end of the sensor testing system.

In an embodiment, the gas supply and pressurization system includes multiple gas cylinders. A gas output end of each gas cylinder is provided with a gas pressure gauge, the gas output end of each gas cylinder is connected to the first pipeline through a pressure-resistant hose, and the pressure-resistant hose is provided with a pressure-reducing valve.

In an embodiment, the pressurized storage tank system includes a pressurized storage tank and a storage tank support. An outer side of the pressurized storage tank is provided with the first insulation layer, and the pressurized storage tank is fixed on the storage tank support.

In an embodiment, the pipeline testing system includes a first pipe section, a return-bending pipe section and a second pipe section. The first pipe section is connected to the second pipe section through the return-bending pipe section, and an outer side of each of the first pipe section, the return-bending pipe section, and the second pipe section is provided with the second insulation layer.

In an embodiment, the reflux pump is a gear pump, and the gear pump is provided with an explosion proof motor.

In an embodiment, the crude oil transportation drag-reducing agent testing loop test bench further includes a safety protection system. The safety protection system includes a harmful gas sensor, a controller, a safety valve, and an alarm.

In a second aspect, the use method of the crude oil transportation drag-reducing agent testing loop test bench includes:
  a process of sucking liquid by the reflux pump to the reflux tank, including: opening the fifth electromagnetic valve, the eighth electromagnetic valve and the ninth manual valve, and starting the reflux pump in a forward direction;
  a process of sucking the liquid by the reflux pump to the pressurized storage tank system, including: opening the second electromagnetic valve and the sixth electromagnetic valve followed by opening the eighth electromagnetic valve, and starting the reflux pump in the forward direction;
  a test medium shear-free transfer process, including: opening the second electromagnetic valve, the fourth electromagnetic valve, the fifth electromagnetic valve and the sixth electromagnetic valve, and ensuring that the eighth manual valve and the ninth manual valve are closed;
  a shear circulation process with the reflux pump, including: opening the second electromagnetic valve, the sixth electromagnetic valve, the seventh electromagnetic valve and the ninth manual valve, and adjusting the reflux pump in the forward direction and a reverse direction according to a liquid volume for cyclic shearing;
  a heating process for mixing liquid in the pressurized storage tank system, including: opening the third electromagnetic valve, the second electromagnetic valve, and the tenth manual valve, and monitoring a temperature display in real time; and
  a testing process.

In an embodiment, the testing process includes a 6 mm testing process, a 12.7 mm testing process, and a 25 mm testing process.

In an embodiment, the 6 mm testing process includes the following steps: confirming that the first, fourth, sixth, eighth, and ninth manual valves are open; supplying liquid and heating; supplying gas and pressurizing; and, after preparation is complete, opening the first electromagnetic valve to start a test.

The 12.7 mm testing process includes the following steps: confirming that the second, fifth, sixth, eighth, and ninth manual valves are open; supplying liquid and heating; supplying gas and pressurizing; and, after preparation is complete, opening the first electromagnetic valve to start the test.

The 25 mm testing process includes the following steps: confirming that the third, seventh, eighth, and ninth manual valves are open; supplying liquid and heating; supplying gas and pressurizing; and, after preparation is complete, opening the first electromagnetic valve to start the test.

The disclosure has the following beneficial effects.

The disclosure can evaluate the performance of drag-reducing agents in transportation pipeline devices within a laboratory setting, and further inspect, evaluate, and test the effective performance of different proportions and types of drag-reducing agents. Additionally, the disclosure also ensures the safety of experimental test, reduces testing costs, avoids the production of large amounts of waste liquid, and minimizes test space. Moreover, the following multiple functions can be achieved.

(1) The frictional resistance of conventional pipeline transportation media such as crude oil and diesel in the pipeline can be tested.

(2) The drag-reducing rate of different types and formulations of drag-reducing agents in the test pipelines can be tested.

(3) The effective flow increase rate of the pipelines for different transportation media can be tested.

(4) The pipeline design allows for the expansion of different processes in subsequent use, enabling other pipeline transportation tests.

(5) The modularity design is used, facilitating disassembly and assembly, minimizing the space required, and making it convenient for overall movement, assembly, and organization.

(6) The automation level control allows for the operation of valves and the reflux pump through software, with real-time display and data acquisition, enhancing the efficiency of testing.

BRIEF DESCRIPTION OF DRAWINGS

In order to provide a clearer explanation of specific embodiments of the disclosure or the technical solutions in the related art, the accompanying drawings required for the specific embodiments or related art description are briefly introduced below. In all the accompanying drawings, similar elements or parts are generally identified by similar reference numerals. In the accompanying drawings, each component or part may not be drawn in actual proportion.

FIG. 6A illustrates a first insulation layer of the heating and insulation testing system, and FIG. 6B illustrates a second insulation layer of the heating and insulation testing system.

DETAILED DESCRIPTION OF EMBODIMENTS

Exemplary embodiments are provided below to illustrate implementations of the disclosure, and those skilled in the art can easily understand other advantages and effects of the disclosure from the content disclosed in the specification. The disclosure can also be implemented or applied through different specific embodiments, and various details in the specification can be modified or changed based on different perspectives and applications without departing from the spirit of the disclosure. It should be noted that, without conflict, the following embodiments and their features can be combined with each other.

In the description of the disclosure, unless otherwise specified, "multiple" means two or more; The terms "up", "down", "left", "right", "inside", "outside", "front end", "back end", "head", and "tail" etc., indicate orientation or positional relationships based on the orientation or positional relationships shown in the accompanying drawings, only for the convenience of describing the disclosure and simplifying the description, and do not indicate or imply that the device or element referred to must have a specific orientation, be constructed and operated in a specific orientation, and therefore cannot be understood as limiting the disclosure. In addition, the terms "first", "second" and "third", etc. are only used for descriptive purposes and cannot be understood as indicating or implying relative importance.

In the description of the disclosure, it should be noted that unless otherwise specified and limited, the term "connected" should be broadly understood, for example, it can be a fixed connection, a detachable connection, or an integral connection; it can be a mechanical connection or an electrical connection; it can be a directly connection or an indirectly connection through an intermediate medium. For those skilled in the art, specific meanings of the above terms in the disclosure can be understood in specific situations.

The specific embodiments of the disclosure are further described in detail with reference to the accompanying drawings and embodiments.

Figure 1:
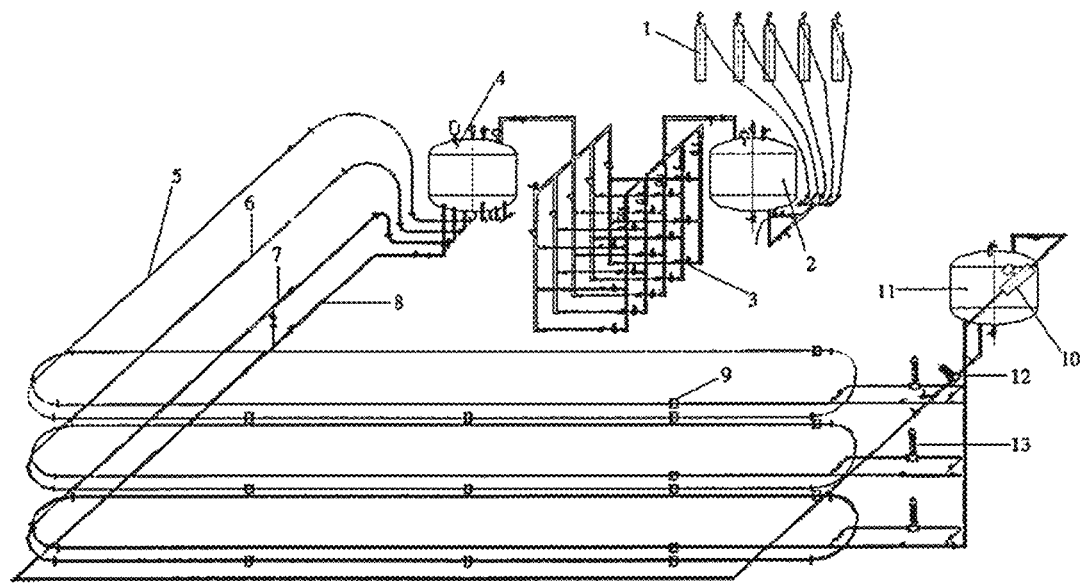
FIG. 1 illustrates a schematic diagram of an indoor testing loop process flow in the related art.
Figure 2:
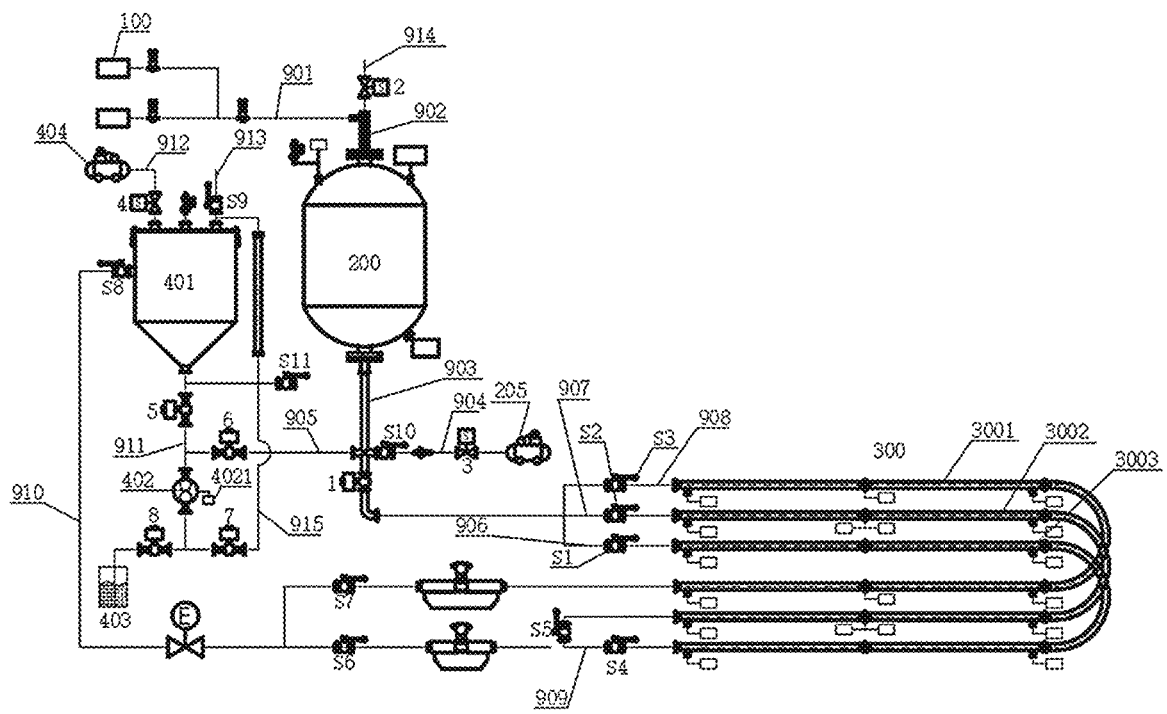
FIG. 2 illustrates a schematic diagram of an overall structure of a crude oil transportation drag-reducing agent testing loop test bench according to an embodiment of the disclosure.

An embodiment of the disclosure provides a crude oil transportation drag-reducing agent testing loop test bench. As shown in FIG. 2, the crude oil transportation drag-reducing agent testing loop test bench includes a gas supply and pressurization system 100, a pressurized storage tank system 200, a pipeline testing system 300, a reflux and circulation system, a valve switching system F, a heating and insulation testing system, and a sensor testing system 600.

Figure 3:
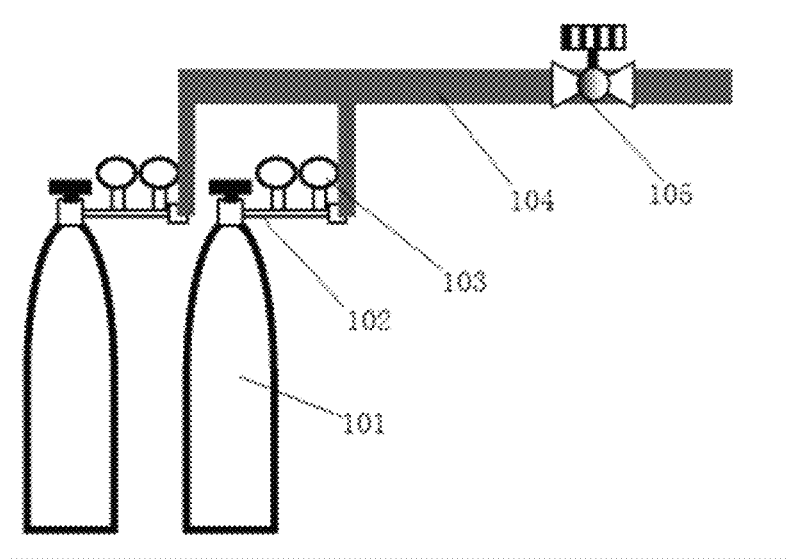
FIG. 3 illustrates a schematic structural diagram of a gas supply and pressurization system of the crude oil transportation drag-reducing agent testing loop test bench according to an embodiment of the disclosure.

As shown in FIG. 3, the gas supply and pressurization system 100 includes multiple gas cylinders 101. A gas output end 102 of each gas cylinder 101 is provided with a gas pressure gauge 103, the gas output end 102 of each gas cylinder 101 is connected to the first pipeline 901 through a pressure-resistant hose 104, and the pressure-resistant hose 104 is provided with a pressure-reducing valve 105.

Exemplarily, to ensure the stability and reliability of pressure during the pressurized testing process and to guarantee a stable gas supply, calculations are made as follows. During the testing process, a maximum exhaust volume required is 200 liters (L), a pressure is 1 MPa, a volume of a standard gas cylinder is 40 L, and a gas supply pressure is 13±0.5 MPa. A brand new set of nitrogen gas cylinders can meet the overall gas supply requirements. During the test, a maximum displacement for displacement testing is 100 liters per minute (L/min), and a maximum pressure is 1.6 MPa. Therefore, an instantaneous gas supply rate needs to reach 1600 L/min under standard conditions. A high-displacement pressure reducer and related process pipelines are required to ensure the stability of the test. Therefore, in the design, to ensure the overall safety and convenience of the test, it is determined to use two sets of gas cylinder groups for gas supply, and the pressure reducer adopts three sets of high-flow pressure reduction devices (SR-12) to meet the needs of instantaneous gas supply and stable testing.

Two sets of gas cylinders connected in parallel are used to supply gas simultaneously, and before the gas finally enters a gas tank, and a set of pressure reducers is added to ensure the stability of the pressure input into the gas tank during high-flow testing.

The gas supply and pressurization system 100 is connected to a second pipeline 902 through a first pipeline 901, the second pipeline 902 is connected to a first end 201 of the pressurized storage tank system 200, and a second end 202 of the pressurized storage tank system 200 is connected to a third pipeline 903, the third pipeline 903 is connected to a fourth pipeline 904, a fifth pipeline 905, a sixth pipeline 906, a seventh pipeline 907, and an eighth pipeline 908, and the fourth pipeline 904 is connected to a first air compressor 205.

Figure 4:
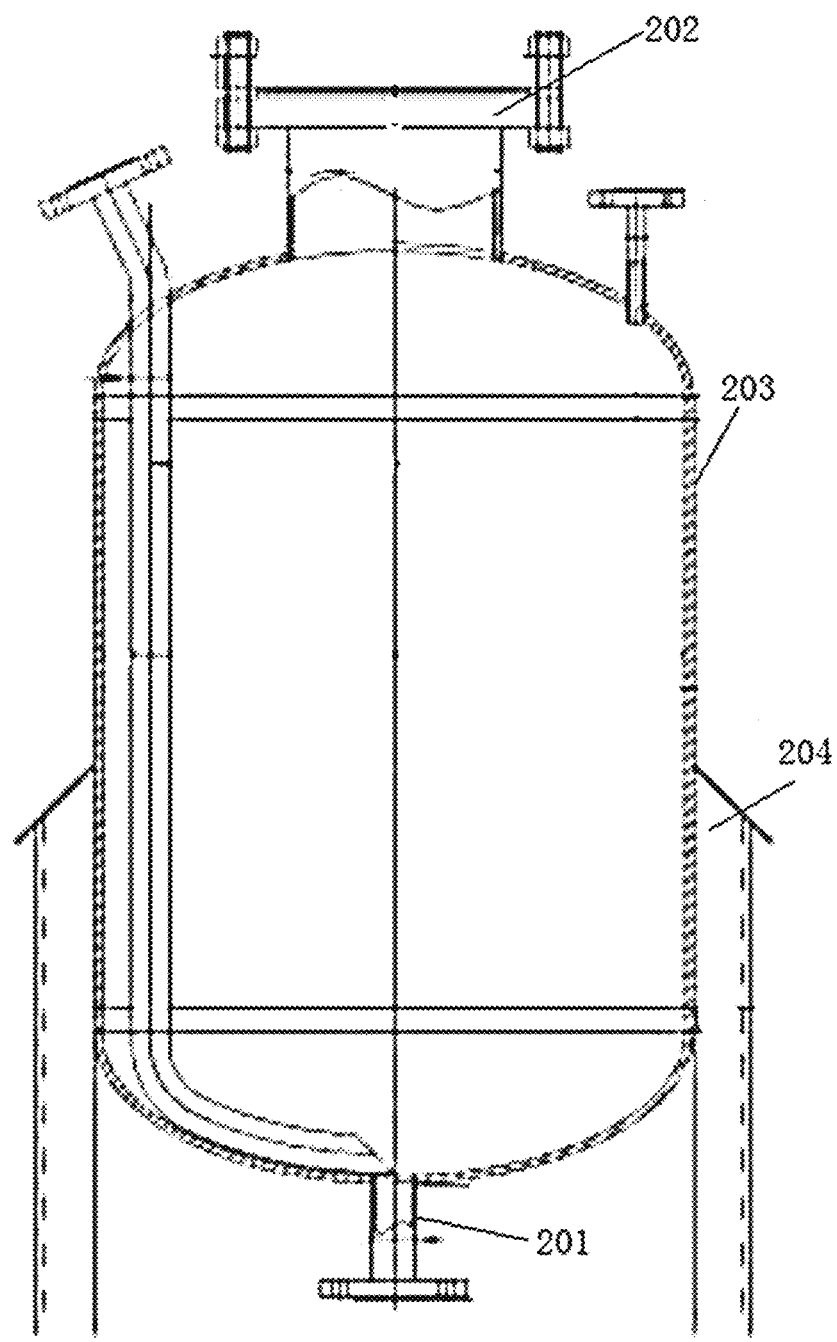
FIG. 4 illustrates a schematic structural diagram of a pressurized storage tank system of the crude oil transportation drag-reducing agent testing loop test bench according to an embodiment of the disclosure.

As shown in FIG. 4, the pressurized storage tank system 200 includes a pressurized storage tank 203 and a storage tank support 204. An outer side of the pressurized storage tank 203 is provided with a first insulation layer 501, and the pressurized storage tank 203 is fixed on the storage tank support 204.

Exemplarily, the pressurized storage tank 203 is designed with a capacity of 100 L and a pressure resistance of 1.6 MPa. Since the test requires the injection of a large amount of gas and subsequent pressurization testing, the pressurized storage tank 203 must be designed and manufactured as a pressure vessel. A pressure vessel qualification certificate is needed to ensure the safety of the test and the stability of the inspection.

The pressurized storage tank 203 is entirely fabricated by welding stainless steel. An opening is defined at a top of the pressurized storage tank 203 (initially determined to be sealed with a φ200 flange with a nominal diameter (DN) of 200 mm), which facilitates gas discharge and pressure relief, as well as internal cleaning. A bottom of the pressurized storage tank 203 is provided with an opening flange of φ50, and multiple pipeline valves are extended to facilitate the circulation testing of the test medium. Inside the pressurized storage tank 203, a uniformly distributed piping system can be installed to ensure that the gas entering from the bottom is relatively evenly distributed through the piping, and enters the test medium at multiple points at the bottom of the pressurized storage tank 203, thereby better achieving the effect of stirring and mixing. The pressurized storage tank 203 adopts a vertical structure and is installed on a movable and fixable support, (with related pipelines and valves, etc., also installed and fixed together, presenting an overall aesthetic and coordinated appearance), allowing for quick setup and mobility for tests.

The pipeline testing system 300 includes three test pipelines consisting of a first test pipeline 3001, a second test pipeline 3002 and a third test pipeline 3003. The sixth pipeline 906, the seventh pipeline 907 and the eighth pipeline 908 are respectively connected to the third test pipeline 3003, the second test pipeline 3002 and the first test pipeline 3001, an end of the second test pipeline 3002 is connected to an end of the third test pipeline 3003 through a ninth pipeline 909, and an end of the first test pipeline 3001 is connected to a tenth pipeline 910.

Figure 5:
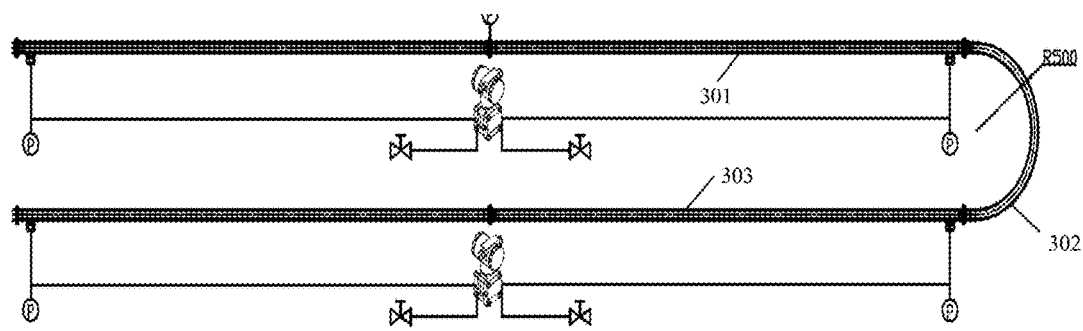
FIG. 5 illustrates a schematic structural diagram of a pipeline testing system of the crude oil transportation drag-reducing agent testing loop test bench according to an embodiment of the disclosure.

As shown in FIG. 5, the pipeline testing system 300 includes a first pipe section 301, a return-bending pipe section 302 and a second pipe section 303. The first pipe section 301 is connected to the second pipe section 303 through the return-bending pipe section 302, and an outer side of each of the first pipe section 301, the return-bending pipe section 302, and the second pipe section 303 is provided with a second insulation layer 502.

The test pipelines consist of three pipelines with different inner diameters, which are as follows: an inner diameter of 25 mm (32 mm×3.5 mm), with an effective test length of 24 meters (m); an inner diameter of 12.7 mm (21 mm×4.15 mm), with an effective test length of 24 m; and an inner diameter of 6 mm (12 mm×3 mm), with an effective test length of 24 m. As shown in FIG. 2.

The test pipelines are equipped with height-adjustable supports to adapt to the actual laboratory room floor, ensuring the levelness of the test pipelines. Positions of differential pressure sensors 603 and pressure sensors 602 can be adjusted to ensure the stability and reliability of the test data.

A pipe return-bending end of the return-bending pipe section 302 has a bending radius of 500 mm, which reduces the impact of the test medium bending on the test data. For the connection between added pipe sections, after considering various factors, a threaded connection method is adopted to ensure the connection is sturdy and reliable.

To facilitate the adjustment and arrangement of the laboratory layout, pressure-resistant hoses are used in the gas supply pipelines, and the reflux and circulation pipelines, and between the pressurized storage tank 203 and the test pipelines, which allows for the adjustment of the layout angle and position.

The reflux and circulation system includes a reflux tank 401 and a reflux pump 402. The tenth pipeline 910 is connected to the reflux tank 401, the reflux tank 401 is connected to a liquid preparation tank 403 through an eleventh pipeline 911, the eleventh pipeline 911 is connected to the fifth pipeline 905, the reflux pump 402 is disposed on the eleventh pipeline 911, the reflux tank 401 is connected to a second air compressor 404 through a twelfth pipeline 912, and an upper end of the reflux tank 401 is provided with a thirteenth pipeline 913.

To facilitate the reflux of the test medium and subsequent cleaning, and the placement and layout arrangement in the laboratory, the reflux tank 401 has a capacity of 120 L and is made of non-metallic material. The reflux tank 401 is equipped with a sealable lid and a pressure balancing valve to prevent the escape of harmful gases and ensure the smooth flow of the circulating medium. The entire reflux and circulation system is provided with an aluminum alloy profile support, which can be used to design and fix components such as the reflux pump 402 together, forming a reflux and displacement module for easy subsequent assembly and process design.

The reflux pump 402 adopts a gear pump. After comprehensive consideration, the reflux pump 402 is preliminarily designed with a displacement of 2 m$^3$/h, an inlet and outlet diameter of 25 mm and a maximum pressure of 1 MPa. The reflux pump 402 can be controlled through a remote computer. The gear pump includes a pump body made of stainless steel material, and high-speed meshing gears with a high shear rate, which can quickly break down the long-chain molecules in the test medium, thus facilitating subsequent tests (an additional reverse process is provided for the test medium to undergo both forward and reverse shear treatment). The gear pump itself has a self-priming function, and through process switching, can serve as a circulation process to clean and treat the test pipelines, ensuring the stability of subsequent tests.

The gear pump is provided with an explosion proof motor 4021, which can efficiently transfer and displace liquids, and be expanded with a variable frequency motor and a corresponding frequency conversion control system, thereby controlling the reflux and circulation flow rate.

The valve switching system F includes: a manual valve group and an electromagnetic valve group.

The manual valve group includes a first manual valve S1, a second manual valve S2, a third manual valve S3, a fourth manual valve S4, a fifth manual valve S5, a sixth manual valve S6, a seventh manual valve S7, an eighth manual valve S8, a ninth manual valve S9, a tenth manual valve S10 and an eleventh manual valve S11. The first manual valve S1, the second manual valve S2 and the third manual valve S3 are respectively disposed on the sixth pipeline 906, the seventh pipeline 907 and the eighth pipeline 908. The fourth manual valve S4 and the fifth manual valve S5 are disposed on a ninth pipeline 909. The sixth manual valve S6, the seventh manual valve S7 and the eighth manual valve S8 are disposed on the tenth pipeline 910. The ninth manual valve S9 is disposed on the thirteenth pipeline 913. The tenth manual valve S10 is disposed on the third pipeline 903. The eleventh manual valve S11 is disposed on a fourteenth pipeline 914 connected to the first pipeline 901.

The electromagnetic valve group includes a first electromagnetic valve 1, a second electromagnetic valve 2, a third electromagnetic valve 3, a fourth electromagnetic valve 4, a fifth electromagnetic valve 5, a sixth electromagnetic valve 6, a seventh electromagnetic valve 7 and an eighth electromagnetic valve 8. The first electromagnetic valve 1 is disposed on the third pipeline 903. The second electromagnetic valve 2 is disposed on the second pipeline 902. The third electromagnetic valve 3 is disposed on the fourth pipeline 904. The fourth electromagnetic valve 4 is disposed on the twelfth pipeline 912. The fifth electromagnetic valve 5 and the eighth electromagnetic valve 8 are disposed on the eleventh pipeline 911. The sixth electromagnetic valve 6 is disposed on the fifth pipeline 905. The seventh electromagnetic valve 7 is disposed on a fifteenth pipeline 915. An end of the fifteenth pipeline 915 is connected to the eleventh pipeline 911, and another end of the fifteenth pipeline 915 is connected to the reflux tank 401.

Figure 6A:
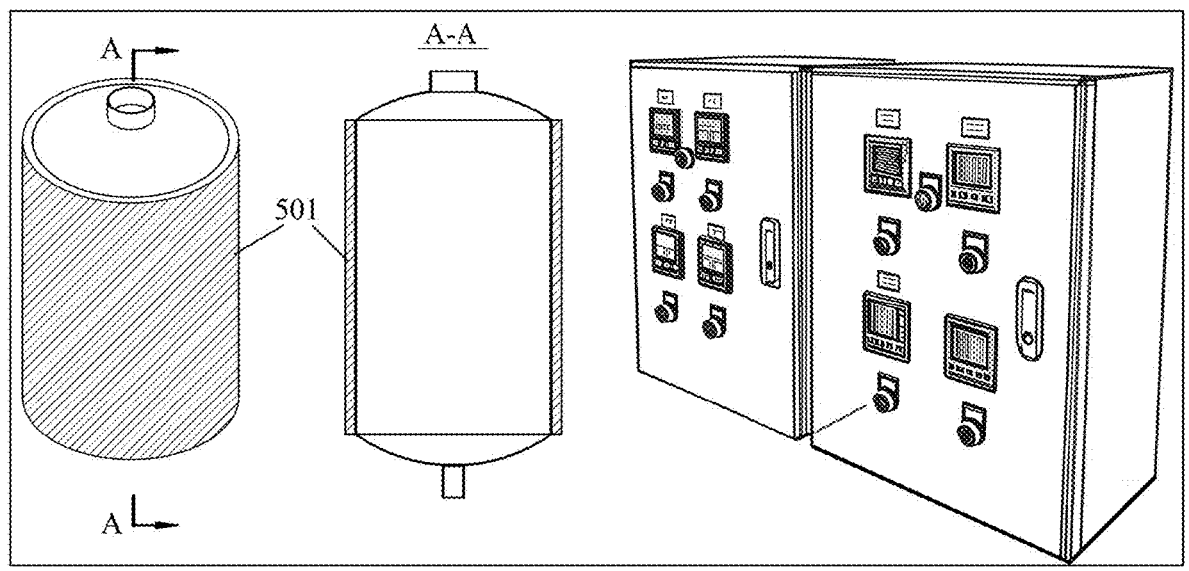
FIG. 6A and FIG. 6B are photographs for illustrating structures of a heating and insulation testing system of the crude oil transportation drag-reducing agent testing loop test bench according to an embodiment of the disclosure; where
Figure 6B:
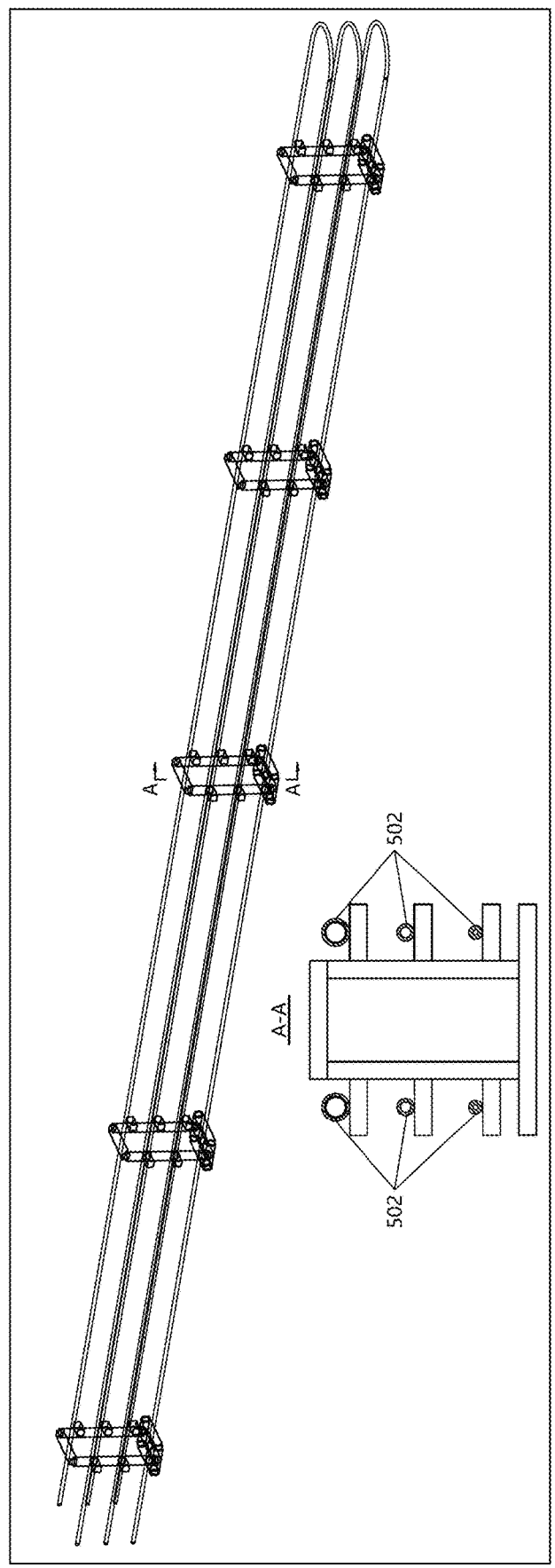

The heating and insulation testing system, as shown in FIG. 6A and FIG. 6B, includes the first insulation layer 501 and the second insulation layer 502. The first insulation layer 501 is disposed on an outer side of the pressurized storage tank system 200, and the second insulation layer 502 is disposed on an outer side of the pipeline testing system 300.

For example, the heating and insulation testing system mainly consists of heating and related temperature collection and control devices, as well as external insulation materials. The exterior of the pressurized storage tank 203 is designed to be neat and smooth, and the heating and insulation system can be added to wrap the pressurized storage tank 203 as needed, so as to heat the test medium, expanding the adaptability range for the test medium. The test temperature range is from room temperature to 100° C., and the heating power is initially designed at 5 kilowatts (kW) with a safe and explosion proof design. The specific design can be adjusted according to the required heating rate. To ensure the test results, the entire pipeline can also be equipped with heating and insulation measures, which are wrapped around the test pipelines as a whole.

Figure 7:
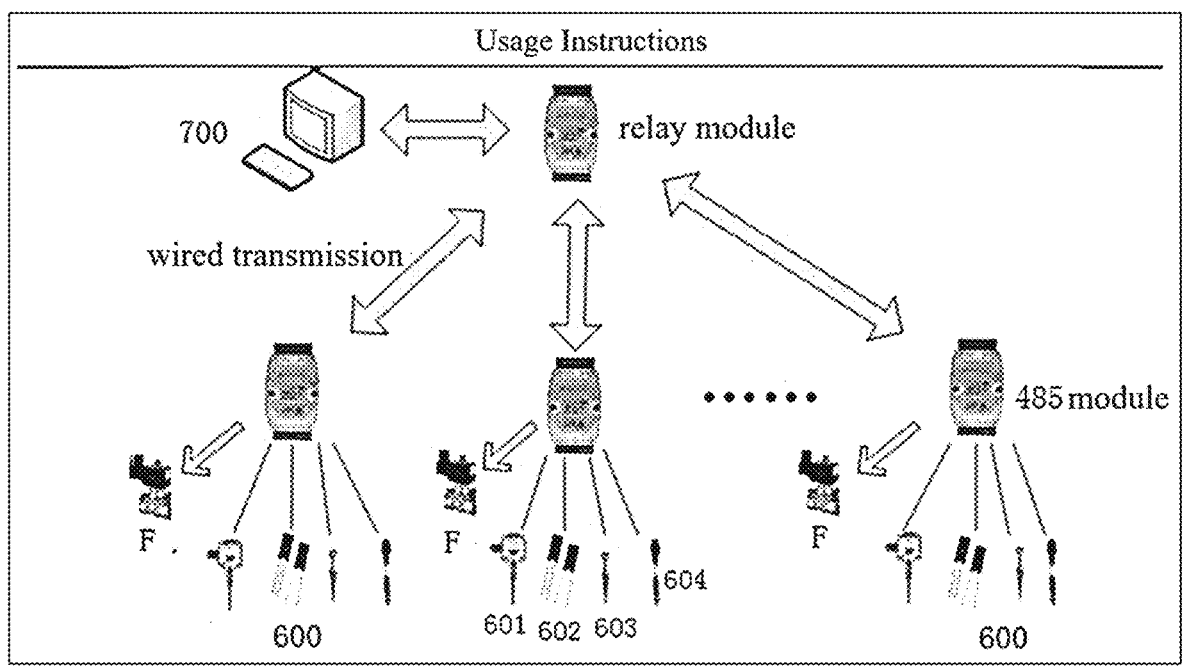
FIG. 7 illustrates a schematic diagram of signal connections for a data acquisition and control system of the crude oil transportation drag-reducing agent testing loop test bench according to an embodiment of the disclosure.

The sensor testing system 600, as shown in FIG. 7, includes temperature sensors 601, pressure sensors 602, differential pressure sensors 603, and a flow sensor 604. The temperature sensors 601, the pressure sensors 602, and the differential pressure sensors 603 are disposed on the pipeline testing system 300 to collect temperature, differential pressure and pressure signals from the test pipelines, and the flow sensor 604 is disposed on the sixth pipeline 906.

The pressure sensors 602 has various specifications. The pressure sensor 602 disposed on the pressurized storage tank 203 has a range of 2 MPa and an accuracy of 0.1%, with the number of 1. The pressure sensors 602 disposed on different pipes have a range of 1 MPa and an accuracy of 0.1%, with the number of 14.

The differential pressure transmitter, i.e., the differential pressure sensor 603, is an intelligent transmitter based on a microprocessor, and outputs corresponding 4 milliamperes (mA) to 20 mA analog signals and digital signals. Its unique automatic correction function for temperature and static pressure errors enables the differential pressure transmitter to meet stringent usage environments. The differential pressure transmitter has a DE communication protocol, which eliminates the transmission errors of the analog signals and facilitates debugging, calibration, and fault diagnosis of the differential pressure transmitter.

The differential pressure and pressure test points are set in stable flow sections of the pipes, with independent venting test ports. According to the process and test design, this prevents the presence of gas bubbles in the pressure measurement pipeline, thereby ensuring that the flow resistance of the test medium can be accurately and stably measured. Based on actual experimental testing, the differential pressure value used in the test pipelines with a diameter of q 25 mm should be below 100 kilopascals (kPa), and thus the differential pressure sensors have a range selected to be 100 kPa, with the number of 2.

Based on actual experimental testing, the differential pressure value used in the test pipelines with a diameter of φ 12.7 mm should be below 200 kPa, and thus the differential pressure sensors have a range selected to be 200 kPa, with the number of 2. All the differential pressure sensors use the Rosemount™ 3051 series.

The temperature sensors 601 are primarily used to measure the temperature of the test medium and use the platinum 100 (PT100) method, which can directly display or transmit data to a computer for collection and control. To ensure stable and accurate flow measurement, a mass flow meter from Shouke Shi Hua (Beijing Sincerity Automatic Equipment Co., Ltd, China) is used as the flow sensor 604, specifically a flow meter with a type number of DMF-1-V15 and a micro-bend rated at 4000 kilograms per hour (kg/h), outputting a 4 mA to 20 mA signal. The range can be adjusted according to needs to 4000 or 6000 kg/h, with an accuracy of 0.1%.

Based on the actual test requirements, the output flow of the test pipeline (φ 25 mm) is connected to a flow meter with a capacity of 6000 kg/h, while the output flow of the test pipeline (φ 6 mm or φ 12.7 mm) is connected to a flow meter with a capacity of 4000 kg/h.

In some embodiments, as shown in FIG. 7, the crude oil transportation drag-reducing agent testing loop test bench further includes a data acquisition and control system 700. A signal output end of the data acquisition and control system 700 is connected to a signal input end of the valve switching system F, and a signal input end of the data acquisition and control system 700 is connected to a signal output end of the sensor testing system 600.

The differential pressure, pressure, flow, temperature, and other signals of the entire test bench are collected through a dedicated acquisition module, and then transmitted to the computer via related professional signals. The computer uses an application program to collect, display, store, and analyze the data, and also performs related controls, such as flow and temperature.

Figure 8:
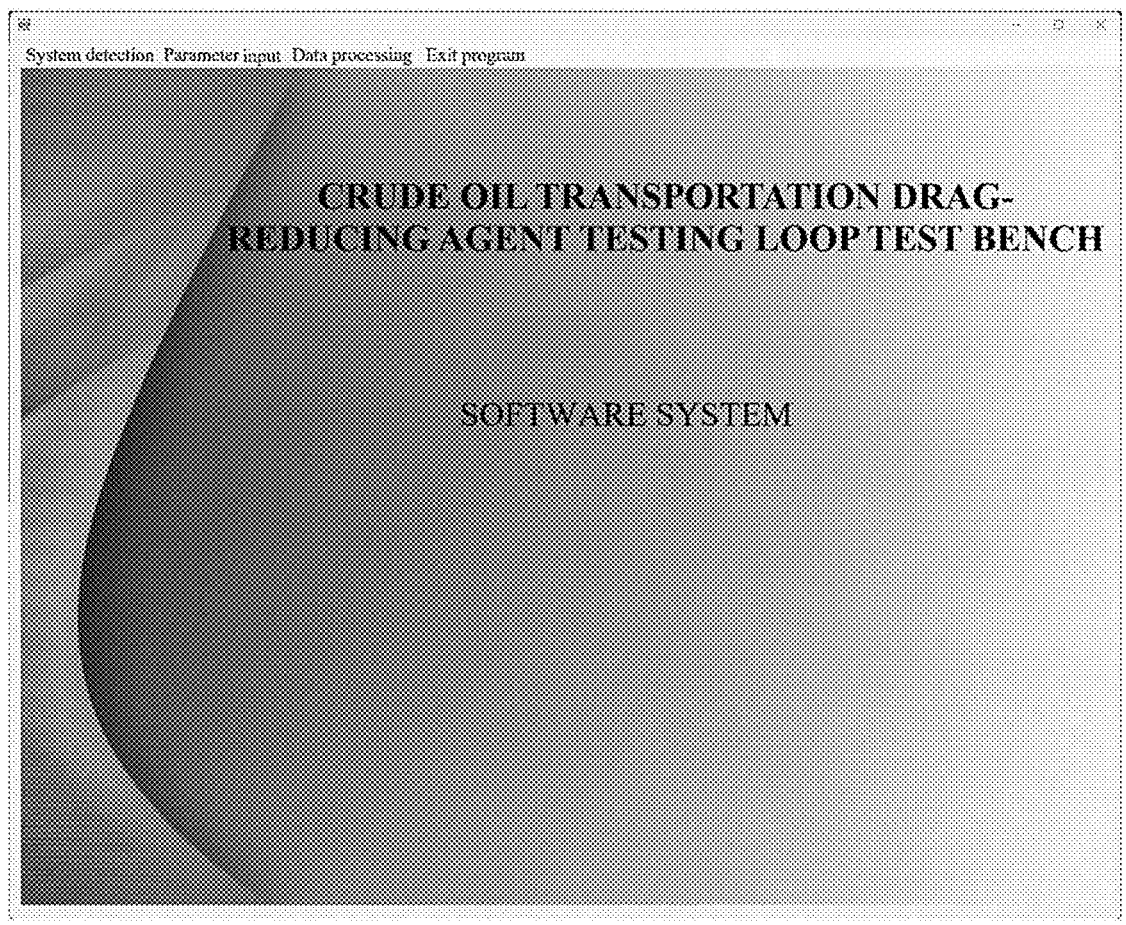
FIG. 8 illustrates a schematic diagram of an interface for clicking to enter a test according to an embodiment of the disclosure.
Figure 9:
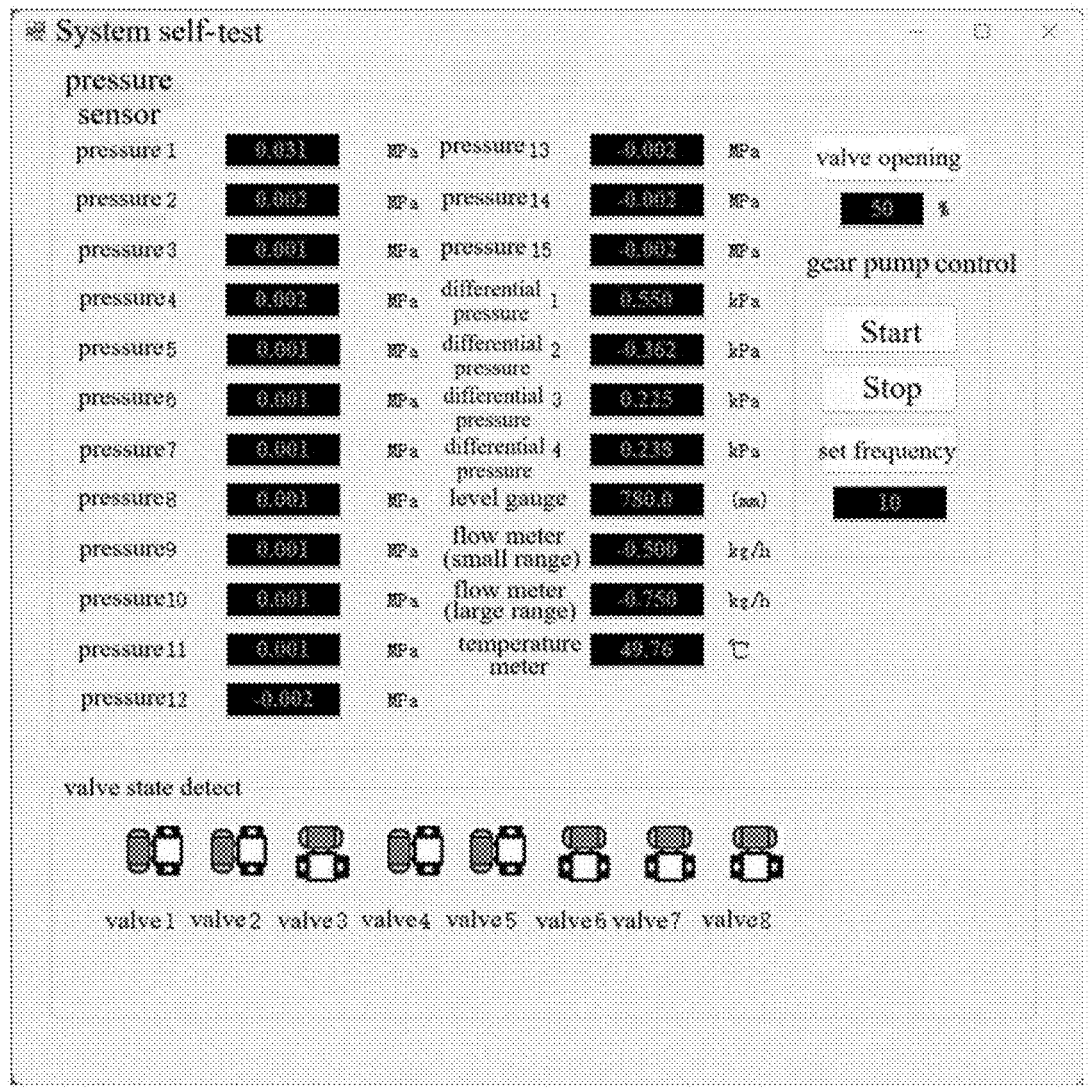
FIG. 9 illustrates a schematic diagram of a system self-check interface according to an embodiment of the disclosure.
Figures 10, 11:
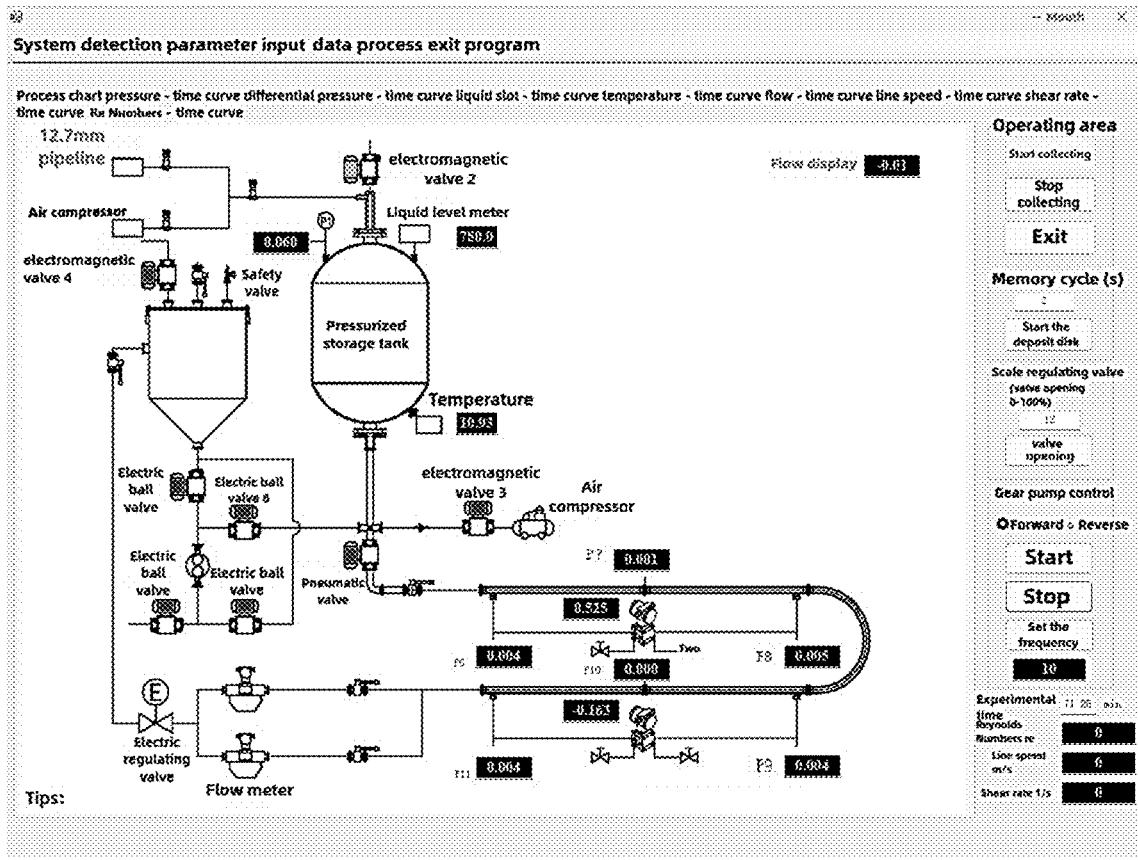
FIG. 10 illustrates a schematic diagram of an interface for inputting test information and determining the test name according to an embodiment of the disclosure.
FIG. 11 illustrates a schematic diagram of entering a test interface and displaying relevant information according to an embodiment of the disclosure.
Figure 12:
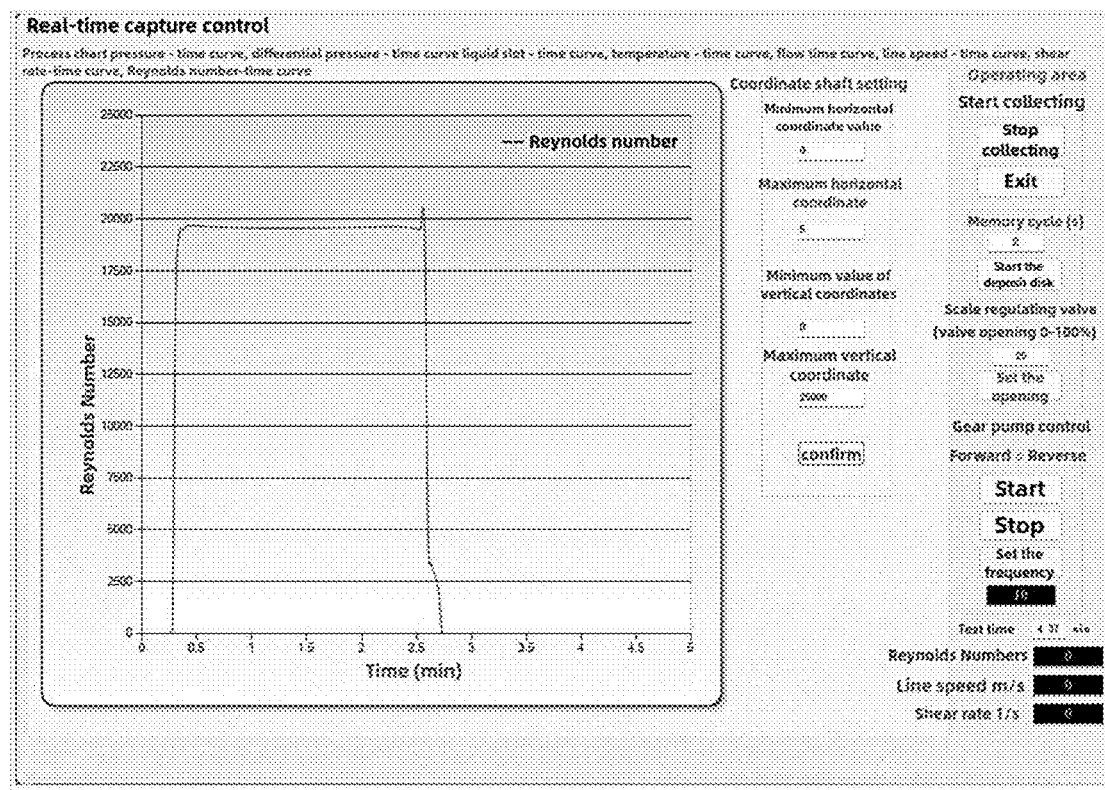
FIG. 12 illustrates a Reynolds number test curve according to an embodiment of the disclosure.
Figure 13:
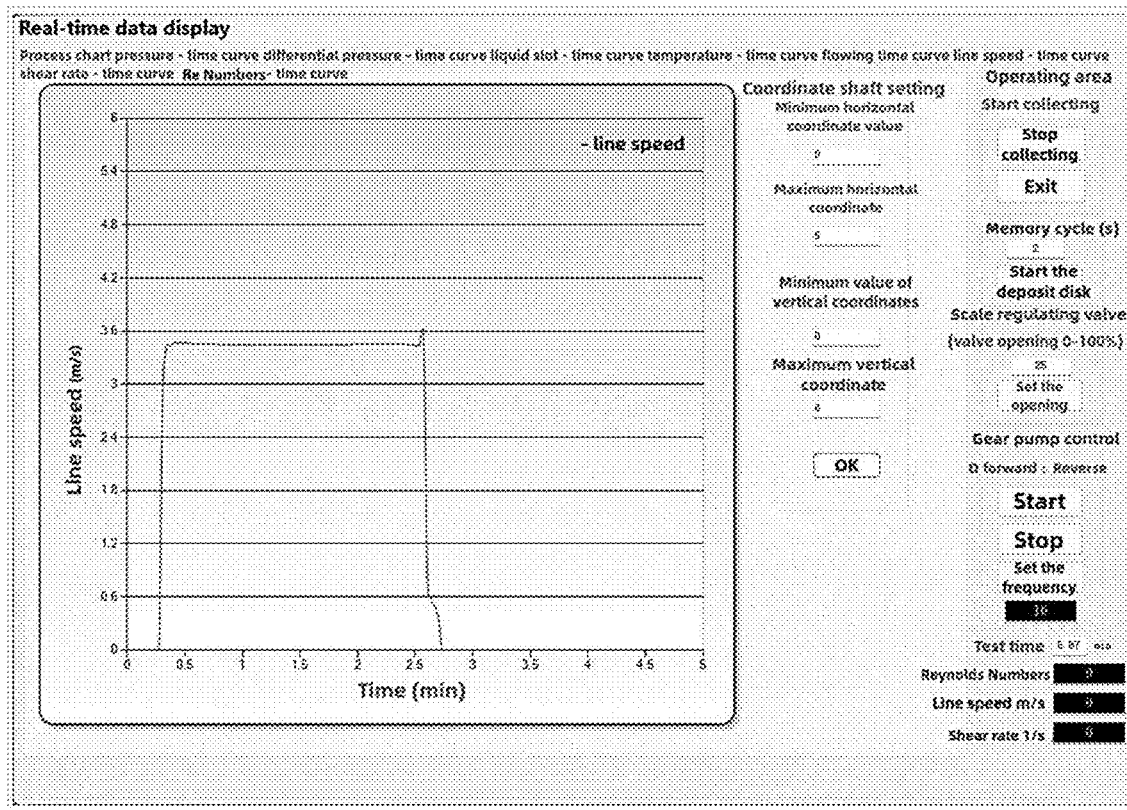
FIG. 13 illustrates a test line speed according to an embodiment of the disclosure.
Figure 14:
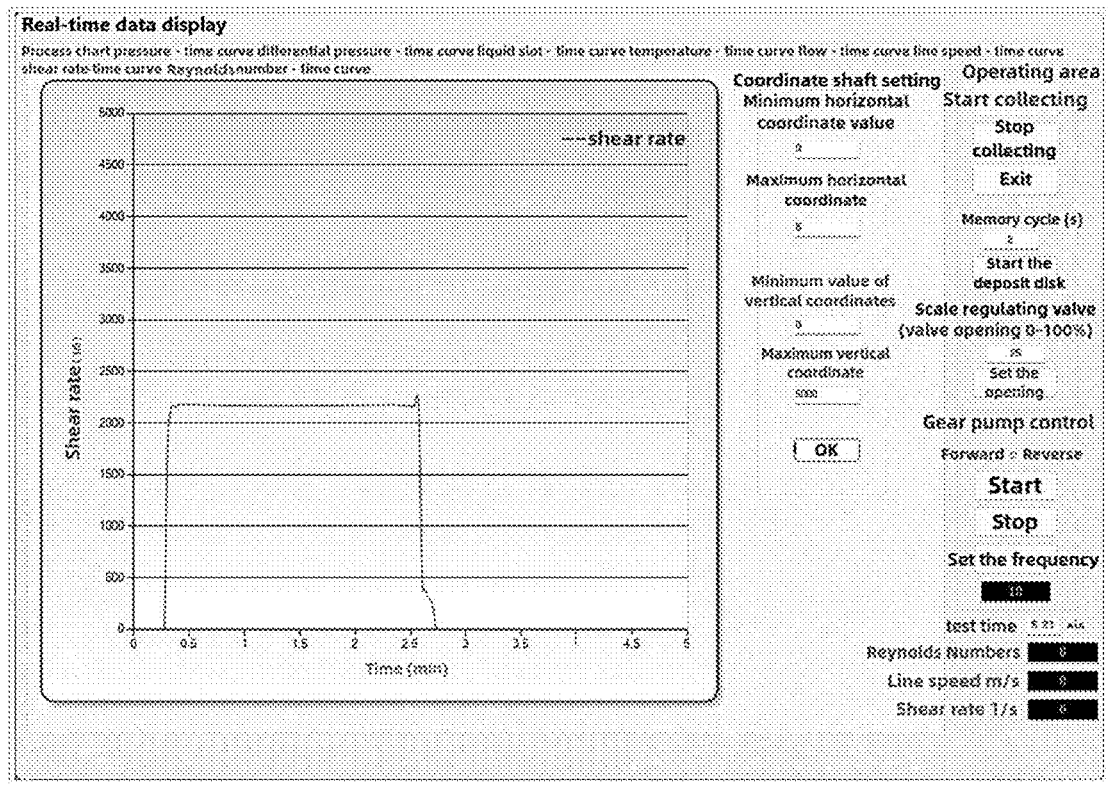
FIG. 14 illustrates a shear rate curve according to an embodiment of the disclosure.

For example, the data acquisition and control system 700 can implement the visualization of the test process based on existing software. As shown in FIG. 8, the test can be entered by clicking the interface. As shown in FIG. 9, the system self-check interface requires confirmation that acquisition values of the relevant sensors are stable and normal. As shown in FIG. 10, the test information is input and the test name is determined. As shown in FIG. 11, the test interface is entered to display relevant information. FIG. 12 to FIG. 14 respectively illustrate the Reynolds number test curve, the test line speed, and the shear rate curve.

Figure 15:
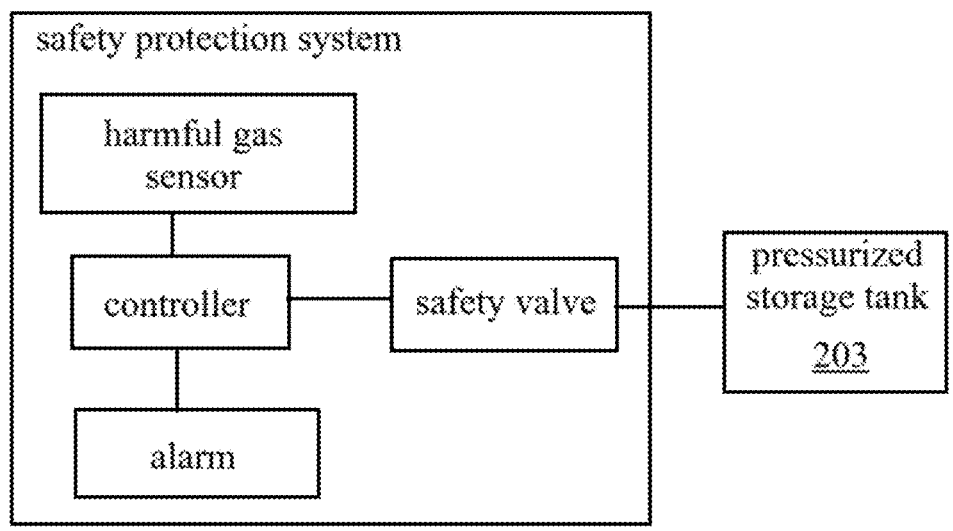
FIG. 15 illustrates a schematic diagram of a safety protection system of the crude oil transportation drag-reducing agent testing loop test bench according to an embodiment of the disclosure.

In some embodiments, the crude oil transportation drag-reducing agent testing loop test bench further includes a safety protection system. Referring to FIG. 15, the safety protection system includes a harmful gas sensor, a controller, a safety valve, and an alarm. Since the test medium or the cleaning medium used in the process may have some volatility, it is necessary to equip the test space, especially the medium circulation control area, with a dedicated harmful gas alarm to ensure test safety. The pressurized storage tank 203 has a large volume and is pressurized by injecting gas, so additional safety valves are required to enhance safety awareness. To prevent various sensor acquisition anomalies during the test, the test bench is equipped with various limit-exceeding alarms, which provide real-time alerts to test personnel to ensure test safety.

The embodiment of the disclosure further provides a use method of the crude oil transportation drag-reducing agent testing loop test bench. The use method includes the following steps 1-3 (if not specifically marked, it is indicated that other valves are in a closed state).

1. A normal experimental test process.

1.1, a certain amount of test medium is calculated and prepared, and all valves in the process are closed.

1.2, power is supplied and all differential pressure, pressure, temperature, and other signals are tested to ensure that the sensors are working properly.

1.3, when conducting a blank test without drag-reducing agent, the gear pump is used to draw liquid into the pressurized storage tank 203. The specific operating steps are as follows: the second electromagnetic valve 2 and the sixth electromagnetic valve 6 are first opened, and finally the eighth electromagnetic valve 8 is opened, and the gear pump is started in a forward direction. When conducting a test with drag-reducing agent, the gear pump is used to draw liquid into the reflux tank 401. The specific operating steps are as follows: the fifth electromagnetic valve 5, the eighth electromagnetic valve 8, and the ninth manual valve S9 are opened, and the gear pump is started in the forward direction.

1.4, if a drag-reducing agent needs to be added, the ninth manual valve S9 is opened to inject the drag-reducing agent into the reflux tank 401, then the ninth manual valve S9 is closed, and a test medium shear-free transfer process is performed. The specific operating steps are as follows: the second electromagnetic valve 2, the fourth electromagnetic valve 4, the fifth electromagnetic valve 5, and the sixth electromagnetic valve 6 are opened (ensure that the eighth manual valve S8 is in the closed state).

1.5, the heating device of the pressurized storage tank 203 is opened and a target test temperature is set to heat the test medium. To ensure even heating, the liquid medium in the storage tank is stirred at regular intervals during the heating process. The specific operating steps are as follows: the third electromagnetic valve 3, the second electromagnetic valve 2, and the tenth manual valve S10 (which can be kept open) are opened, and the temperature display is monitored in real time.

1.6, after the liquid medium reaches the target temperature, the gas supply channel is opened to pressurize the pressurized storage tank 203.

1.7, after the software checks that the test is normal, the experimental test is proceeded and relevant data is collected and stored in real time. The operating steps for different pipeline test processes are as follows.

A 6 mm testing process includes: confirming that the first manual valve S1, the fourth manual valve S4, the sixth manual valve S6, the eighth manual valve S8, and the ninth manual valve S9 are open, supplying liquid and heating, supplying gas and pressurizing, and after preparation is complete, opening the first electromagnetic valve 1 to start the test.

A 12.7 mm testing process includes: confirming that the second manual valve S2, the fifth manual valve S5, the sixth manual valve S6, the eighth manual valve S8, and the ninth manual valve S9 are open, supplying liquid and heating, supplying gas and pressurizing, and after preparation is complete, opening the first electromagnetic valve 1 to start the test.

A 25 mm testing process includes: confirming that the third manual valve S3, the seventh manual valve S7, the eighth manual valve S8, and the ninth manual valve S9 are open, supplying liquid and heating, supplying gas and pressurizing, and after preparation is complete, opening the first electromagnetic valve 1 to start the test.

1.8, according to the specific test requirements for testing the flow increase rate or drag-reducing rate, the opening of control valve is adjusted based on an actual flow rate collected to ensure stable test conditions.

1.9, after the test is successfully completed, the test data is organized and the test medium is cleaned up.

2. A test process of reflux and circulation process.

2.1, all valves in the process are closed.

2.2, if continuing with the current test, the medium is transferred from the reflux tank 401 to the pressurized storage tank 203 by the test medium shear-free transfer process, as described in 1.4. If adding a new drag-reducing agent for a next test, a gear pump shear circulation process is used to cyclic shear the drag-reducing agent. The specific operating steps are as follows: the second electromagnetic valve 2, the sixth electromagnetic valve 6, the seventh electromagnetic valve 7, and the ninth manual valve S9 are opened, and the gear pump is adjusted in the forward and reverse directions according to the liquid volume for cyclic shearing.

2.3, the test medium is sampled in real time and relevant physical properties are tested until the medium meets the requirements for subsequent tests.

2.4, the test medium is transferred completely to the pressurized storage tank 203 by the reflux pump 402, the test process is adjusted, and the test pipelines are cleaned.

3. A pipeline cleaning process.

3.1, all the valves in the process are closed.

3.2, a portion of cleaning solvent medium is added into the reflux tank 401 (diesel or other solvents can generally be used).

3.3, pipeline cleaning is performed, which is the same as the test process described in 1.9;

3.4, after the pipeline cleaning is completed, a reference test medium is used to conduct a baseline test on the pipelines to ensure that inner walls of the test pipelines are restored to an initial condition.

The embodiments listed in the disclosure are only intended to illustrate the disclosure and are not intended to limit its scope. Those skilled in the art can make various changes and modifications without departing from the spirit and scope of the disclosure. Therefore, all equivalent technical solutions also belong to the scope of the disclosure, and the scope of patent protection of the disclosure should be limited by the claims.

What is claimed is:

1. A crude oil transportation drag-reducing agent testing loop test bench, comprising:
   a gas supply and pressurization system;
   a pressurized storage tank system, wherein the gas supply and pressurization system is connected to a second pipeline through a first pipeline, the second pipeline is connected to a first end of the pressurized storage tank system, and a second end of the pressurized storage tank system is connected to a third pipeline, the third pipeline is connected to a fourth pipeline, a fifth pipeline, a sixth pipeline, a seventh pipeline, and an eighth pipeline, and the fourth pipeline is connected to a first air compressor;
   a pipeline testing system, comprising: a first test pipeline, a second test pipeline and a third test pipeline, wherein the sixth pipeline, the seventh pipeline and the eighth pipeline are respectively connected to the third test pipeline, the second test pipeline and the first test pipeline, and the first test pipeline, second test pipeline, and third test pipeline are connected to a tenth pipeline;
   a reflux and circulation system, comprising: a reflux tank and a reflux pump, wherein the tenth pipeline is connected to the reflux tank, the reflux tank is connected to a liquid preparation tank through an eleventh pipeline, the eleventh pipeline is connected to the fifth pipeline, the reflux pump is disposed on the eleventh pipeline, the reflux tank is connected to a second air compressor through a twelfth pipeline, and an upper end of the reflux tank is provided with a thirteenth pipeline;
   a valve switching system, comprising: a manual valve group and an electromagnetic valve group;
      wherein the manual valve group comprises a first manual valve, a second manual valve, a third manual valve, a fourth manual valve, a fifth manual valve, a sixth manual valve, a seventh manual valve, an eighth manual valve, a ninth manual valve, a tenth manual valve and an eleventh manual valve, the first manual valve, the second manual valve and the third manual valve are respectively disposed on the sixth pipeline, the seventh pipeline and the eighth pipeline, the fourth manual valve and the fifth manual valve are disposed on a ninth pipeline, the sixth manual valve, the seventh manual valve and the eighth manual valve are disposed on the tenth pipeline, the ninth manual valve is disposed on the thirteenth pipeline, the tenth manual valve is disposed on the third pipeline, and the eleventh manual valve is disposed on a fourteenth pipeline connected to the first pipeline;
      wherein the electromagnetic valve group comprises a first electromagnetic valve, a second electromagnetic valve, a third electromagnetic valve, a fourth electromagnetic valve, a fifth electromagnetic valve, a sixth electromagnetic valve, a seventh electromagnetic valve and an eighth electromagnetic valve, the first electromagnetic valve is disposed on the third pipeline, the second electromagnetic valve is disposed on the second pipeline, the third electromagnetic valve is disposed on the fourth pipeline, the fourth electromagnetic valve is disposed on the twelfth pipeline, the fifth electromagnetic valve and the eighth electromagnetic valve are disposed on the eleventh pipeline, the sixth electromagnetic valve is disposed on the fifth pipeline, the seventh electromagnetic valve is disposed on a fifteenth pipeline, an end of the fifteenth pipeline is connected to the eleventh pipeline, and another end of the fifteenth pipeline is connected to the reflux tank;
   a heating and insulation testing system, comprising a first insulation layer and a second insulation layer, wherein the first insulation layer is disposed on an outer side of the pressurized storage tank system, and the second insulation layer is disposed on an outer side of the pipeline testing system; and
   a sensor testing system, comprising temperature sensors, pressure sensors, differential pressure sensors, and a flow sensor, the temperature sensors, the pressure sensors, and the differential pressure sensors are disposed on the pipeline testing system to collect temperature, differential pressure and pressure signals from the first, second and third test pipelines, and the flow sensor is disposed on the sixth pipeline.

2. The crude oil transportation drag-reducing agent testing loop test bench as claimed in claim 1, further comprising: a data acquisition and control system; wherein a signal output end of the data acquisition and control system is connected to a signal input end of the valve switching system, and a signal input end of the data acquisition and control system is connected to a signal output end of the sensor testing system.

3. The crude oil transportation drag-reducing agent testing loop test bench as claimed in claim 1, wherein the gas supply and pressurization system comprises a plurality of gas cylinders, a gas output end of each of the plurality of gas cylinders is provided with a gas pressure gauge, the gas output end is connected to the first pipeline through a pressure-resistant hose, and the pressure-resistant hose is provided with a pressure-reducing valve.

4. The crude oil transportation drag-reducing agent testing loop test bench as claimed in claim 1, wherein the pressurized storage tank system comprises a pressurized storage tank and a storage tank support, an outer side of the pressurized storage tank is provided with the first insulation layer, and the pressurized storage tank is fixed on the storage tank support.

5. The crude oil transportation drag-reducing agent testing loop test bench as claimed in claim 1, wherein the pipeline testing system comprises a first pipe section, a return-bending pipe section and a second pipe section, the first pipe section is connected to the second pipe section through the return-bending pipe section, and an outer side of each of the first pipe section, the return-bending pipe section, and the second pipe section is provided with the second insulation layer.

6. The crude oil transportation drag-reducing agent testing loop test bench as claimed in claim 1, wherein the reflux pump is a gear pump, and the gear pump is provided with an explosion proof motor.

7. The crude oil transportation drag-reducing agent testing loop test bench as claimed in claim 1, further comprising: a safety protection system; wherein the safety protection system comprises a harmful gas sensor, a controller, a safety valve, and an alarm.

8. A use method of the crude oil transportation drag-reducing agent testing loop test bench as claimed in claim 1, comprising:

a process of sucking liquid by the reflux pump to the reflux tank, comprising: opening the fifth electromagnetic valve, the eighth electromagnetic valve and the ninth manual valve, and starting the reflux pump in a forward direction;

a process of sucking the liquid by the reflux pump to the pressurized storage tank system, comprising: opening the second electromagnetic valve and the sixth electromagnetic valve followed by opening the eighth electromagnetic valve, and starting the reflux pump in the forward direction;

a test medium shear-free transfer process, comprising: opening the second electromagnetic valve, the fourth electromagnetic valve, the fifth electromagnetic valve and the sixth electromagnetic valve, and ensuring that the eighth manual valve and the ninth manual valve are closed;

a shear circulation process with the reflux pump, comprising: opening the second electromagnetic valve, the sixth electromagnetic valve, the seventh electromagnetic valve and the ninth manual valve, and adjusting the reflux pump in the forward direction and a reverse direction according to a liquid volume for cyclic shearing; and a heating process for liquid mixing in the pressurized storage tank system, comprising: opening the third electromagnetic valve, the second electromagnetic valve, and the tenth manual valve, and monitoring a temperature display in real time.

\* \* \* \* \*